United States Patent
Li et al.

(10) Patent No.: US 9,921,159 B2
(45) Date of Patent: Mar. 20, 2018

(54) SPLICED DETECTION APPARATUS FOR SIMULTANEOUS WIDE-RANGE IN-SITU DETECTION OF DISSOLVED OXYGEN IN SLUDGE-WATER INTERFACE AND DETECTION METHOD THEREFOR

(71) Applicants: Nanjing Institute of Environmental Sciences, Ministry of Environmental Protection, P. R. C., Nanjing, Jiangsu Province (CN); Chongqing University of Arts and Sciences, Chongqing (CN)

(72) Inventors: Weixin Li, Nanjing (CN); Wenlin Wang, Nanjing (CN); Qiang Li, Chongqing (CN); Bo Liu, Nantong (CN); Yinjing Wan, Nanjing (CN); Ruiming Han, Nanjing (CN); Xiaoyan Tang, Nanjing (CN); Wenjing Li, Nanjing (CN); Fei He, Nanjing (CN); Wei Zhuang, Nanjing (CN); Changxin Zou, Nanjing (CN); Aiping Liu, Nanjing (CN); Shoujing Yin, Beijing (CN); Xiaohan Li, Beijing (CN); Guoquan Pan, Nanjing (CN)

(73) Assignees: Nanjing Institute of Enviormental Sciences, Ministry of Environmental Protection, P.R.C., Nanjing (CN); Chongqing University of Arts and Sciences, Chongqing (CN)

( * ) Notice: Subject to any disclaimer, the term of this patent is extended or adjusted under 35 U.S.C. 154(b) by 0 days.

(21) Appl. No.: 15/331,186

(22) Filed: Oct. 21, 2016

(65) Prior Publication Data

US 2017/0219491 A1    Aug. 3, 2017

(30) Foreign Application Priority Data

Feb. 3, 2016 (CN) .......................... 2016 1 00757684

(51) Int. Cl.
*G01N 21/64* (2006.01)
*G01N 33/18* (2006.01)

(52) U.S. Cl.
CPC ......... *G01N 21/645* (2013.01); *G01N 21/643* (2013.01); *G01N 33/1886* (2013.01);
(Continued)

(58) Field of Classification Search
CPC ............. G01N 21/645; G01N 33/1886; G01N 21/643; G01N 2021/6484; G01N 2021/6432
(Continued)

(56) References Cited

U.S. PATENT DOCUMENTS

| 2007/0140921 A1* | 6/2007 | Mitchell | ............... B65D 51/24 422/400 |
| 2013/0046164 A1* | 2/2013 | Liu | .................... A61B 5/14503 600/364 |

* cited by examiner

Primary Examiner — Seung C Sohn
(74) Attorney, Agent, or Firm — Hauptman Ham, LLP

(57) ABSTRACT

A spliced detection apparatus for simultaneous wide-range in-situ detection of dissolved oxygen in a sludge-water interface of the present invention comprises a dissolved oxygen shimmer host, several detection probes, a casing and detection kits, several vertically through seat chambers being disposed in the casing, the detection kits can be placed and fixed in the seat chambers, the detection kits may be placed on the sludge-water interface, and each detection kit is provided with a vertically through water passage chamber, while the front side face and the back side face of the detection kit are respectively provided with several front slots and rear slots horizontally extending into the detection kit respectively, the detection apparatus further comprises tabs, with probe grooves being provided on the tabs, each detection probe can be put into the probe groove of the corresponding tab and fixed therein, the tabs may be inserted (Continued)

either into the front slots or the rear slots and can enable the probe tips of the detection probes to be placed in the water passage chamber, the detection apparatus can carry out simultaneous wide-range detection of the dissolved oxygen at different heights and horizontal positions of the sludge-water interface, and thus is quick and convenient for use.

10 Claims, 11 Drawing Sheets

(52) U.S. Cl.
CPC ............... *G01N 2021/6432* (2013.01); *G01N 2021/6484* (2013.01)

(58) Field of Classification Search
USPC .................................................. 250/227.11
See application file for complete search history.

US 9,921,159 B2

1

SPLICED DETECTION APPARATUS FOR SIMULTANEOUS WIDE-RANGE IN-SITU DETECTION OF DISSOLVED OXYGEN IN SLUDGE-WATER INTERFACE AND DETECTION METHOD THEREFOR

TECHNICAL FIELD

The present invention relates to the technical field of dissolved oxygen detection apparatus, and more particularly to a spliced detection apparatus for simultaneous wide-range in-situ detection of dissolved oxygen in a sludge-water interface and a detection method therefor.

BACKGROUND ART

Dissolved oxygen shimmer is a one-dimensional microprobe technique for realizing detection of dissolved oxygen concentration at a certain point in the sludge-water interface. It is an optical fiber information exchange sensor based on a fluorescence quenching principle; since oxygen is a natural quencher for some fluorescent indicators, oxygen-sensitive fluorescent indicators are made into oxygen sensing membranes coupled to the end part of the optical fiber; high-brightness light-emitting diodes are used as a light source and miniature photodiode detection system, the oxygen concentration is determined by the optical fiber-conducting fluorescence quenching intensity; a ruthenium complex, with the characteristics of insensitivity to stirring and resistance to the interference of $H_2S$, $CO_2$ and salinity, is so far the most widely used oxygen-sensitive fluorescent indicator.

A current method for the dissolved oxygen determination in the sludge-water interface comprises the following steps: taking a sample of the sludge-water interface from the water area to be detected into a detection container, then fixing a dissolved oxygen shimmer probe on the upper portion of the container, and controlling a fluorescent probe tips on the probe to downwardly extend into the sludge-water interface for determination.

This method has the following disadvantages:
1. The detection range is small, which means that only the data of dissolved oxygen about the sludge-water interface around the dissolved oxygen shimmer probe can be collected at one time;
2. In-situ determination cannot be achieved, but rather, samples of the sludge-water interface need to be taken into the detection container, which can easily lead to changes in the natural environment around the sludge-water interface, resulting in inconsistence of the dissolved oxygen situation of the sampled sludge-water interface with the actual situation;
3. Only one dissolved oxygen shimmer probe can be controlled to detect the dissolved oxygen situation of one position at a certain height in the sludge-water interface each time; the dissolved oxygen situation of the position at other heights or the dissolved oxygen situations of other positions at the same height can only be detected by multiple-time detection which, however, takes a larger time span, may not reflect the real situation; and
4. The height of the probe to the sludge-water interface needs to be controlled by mechanical operation which will easily get damaged, causing time-and-effort consuming operation and inconvenient detection.

SUMMARY OF THE INVENTION

The present invention is intended to solve the technical problem, and provide a spliced detection apparatus for simultaneous wide-range in-situ detection of dissolved oxygen in a sludge-water interface for the state of the prior art and a detection method therefor.

The spliced detection apparatus for simultaneous wide-range in-situ detection of dissolved oxygen in the sludge-water interface comprises a dissolved oxygen shimmer host, the dissolved oxygen shimmer host is connected to several detection probes, the detection probes can extend out probe tips for detecting dissolved oxygen, and the spliced detection apparatus is characterized in that the detection apparatus further comprises a casing and detection kits; the casing is disposed therein with several vertically through seat chambers, in which the detection kits can be placed and fixed; the casing is provided with several horizontally through casing front slots and casing rear slots respectively at the front side and the rear side of each seat chamber, which have correspondingly matching number and height; each of the detection kits is provided with a vertically through water passage chamber, and the front side face and the back side face of the detection kit are respectively provided with several detection kit front slots and detection kit rear slots horizontally extending into the detection kit; when the detection kit is fixed in the seat chamber, the casing front slots and the detection kit front slots are aligned, and the casing rear slots and the detection kit rear slots are aligned; when the casing is placed on the sludge-water interface, the lower portion of the detection kit placed in the seat chamber also comes into contact with the sludge-water interface, and both the detection kit front slots and the detection kit rear slots are in communication with the water passage chamber; the detection apparatus further comprises tabs, which is provided thereon with probe grooves having a profile adapt to the profile of the detection probes; each detection probe can be put into the probe groove of the corresponding tab and fixed therein; the tabs can be inserted through the casing slots into the detection kit slots and can enable the probe tips of the detection probes to be placed in the water passage chamber; when two tabs are respectively inserted into the detection kit front slot and the detection kit rear slot at the same height, the detection apparatus can detect the dissolved oxygen in different horizontal positions at the same height of the sludge-water interface; when the two tabs are inserted into the detection kit front slots or the detection kit rear slots at different heights, and with the same depth, the detection apparatus can detect the dissolved oxygen of the same horizontal position at different heights of the sludge-water interface; simultaneous detection on different positions of the sludge-water interface can be achieved by fixing several detection kits within the casing.

In order to optimize the above technical solution, furthermore, the following specific measures are taken, including: the casing is provided with a fixing shoulder on the upper portion of each seat chamber, and accordingly, the upper end of the detection kit is provided with a boss body which is clamped on the fixing shoulder so as to fix the detection kit into the seat chamber.

Left and right sides of the casing are provided with a coupling convex and a coupling concave respectively, different casings can be connected and fixed together through the clamping between the coupling convex and the coupling concave, thus forming a casing assembly, and increasing the detection range in the sludge-water interface.

A fixing convex is disposed in each of the detection kit front slot and the detection kit rear slot, and slip teeth are disposed at the edges of each tab; when the tab is inserted into the detection kit front slot or the detection kit rear slot, the depth of the tab inserted into the slot may be adjusted by selecting different slip teeth for clamping with the fixing convex.

The tabs are marked with scales, and the depth of the tabs inserted into the slots can be read out from the scales.

Each of the detection probes comprises a flexible optical fiber and a rigid optical fiber (i.e. the probe tip), and the rear end of the rigid optical fiber is connected to the dissolved oxygen shimmer host through the flexible optical fiber.

Each of the detection probes further comprises a probe tip pushing structure, and the probe tip pushing structure comprises a pushing tube, a pushing column, a friction block, a seal ring, a pushing handle and a tube rear seat, wherein the pushing handle is connected to the rear end of the pushing column, while the front end of the pushing column extends into the pushing tube to be fixedly connected to the friction block in the pushing tube; the friction block frictionally engages with the inner wall of the pushing tube, and the tube rear seat plugs the rear end of the pushing tube, the friction block is fixedly connected to the rear portion of the probe tip, and the seal ring is fixed in the pushing tube to separate a chamber of the pushing tube into a front chamber and a rear chamber in a sealing manner, with the front chamber being provided with a through window through which water can enter the front chamber, and accordingly, each probe groove is provided with a groove window at the position corresponding to the through window; when the tab for fixing the detection probe is positioned in the water passage chamber, the through window is in communication with the water passage chamber through the groove window; when an external force for pushing the pushing handle is greater than the frictional force between the friction block and the pushing tube, the friction block slides within the pushing tube, so that the probe tip extends into the front chamber.

The flexible optical fiber is fixedly connected to the pushing handle.

The detection method for simultaneous wide-range in-situ detection of dissolved oxygen in the sludge-water interface comprises the following steps:

step a, assembling a detection apparatus: based on the size of the sludge-water interface to be detected, selecting casings and detection kits of appropriate numbers, fixedly connecting the casings in turn, placing and fixing the detection kits in seat chambers of the casings to ensure that corresponding casing front slots and detection kit front slots are aligned, while casing rear slots and detection kit rear slots are aligned, then selecting several detection probes as needed, clamping each detection probe into the probe groove of the corresponding tab to ensure that the detection probes and the tabs are positioned;

step b, detecting the dissolved oxygen of different horizontal positions at the same height of the sludge-water interface: selecting a pair of the detection kit front slot and the detection kit rear slot at the same height, and respectively enabling the tabs to insert through the corresponding casing slots into the detection kit front slot and the detection kit rear slot, so as to push the probe tip of each of the detection probes to the front chamber of the pushing tube; depositing the assembled casing onto the sludge-water interface, injecting water into the water passage chamber and the front chamber of the pushing tube, and collecting the data of dissolved oxygen in water through each probe tip;

step c, detecting the dissolved oxygen at different heights in the same horizontal position of the sludge-water interface: selecting several detection kit front slots and/or detection kit rear slots, positioned at different heights, respectively enabling the tabs to insert through the corresponding casing slots into the selected detection kit front slots and/or detection kit rear slots, adjusting the depth of the tabs inserted into the detection kit front slots and/or the detection kit rear slots, then pushing the probe tip of each of the detection probes to the front chamber of the pushing tube to enable each of the probe tips to be positioned at different heights in the same horizontal position, depositing the assembled casing onto the sludge-water interface, injecting water into the water passage chamber and the front chamber of the pushing tube, and collecting the data of dissolved oxygen in water through each probe tip;

step d, simultaneously detecting the dissolved oxygen at different horizontal positions and different heights of the sludge-water interface: simultaneously performing step b and step c;

step e, transmitting the data of dissolved oxygen collected by the probe tips in step b, step c and step d to the dissolved oxygen shimmer host, and the dissolved oxygen shimmer host performing analysis treatment on the data and then displaying the data; and step f, lifting the casings from water and taking out the tabs after detection, wherein the method for taking out the tabs comprises the following steps of pulling the pushing handle backwards, so that the friction block slides backwards, when the friction block slides to the rear end of the pushing tube, enabling the probe tips to be retracted into the rear chamber of the pushing tube, continuously pulling the pushing handle backwards to enable the friction block to push against the tube rear seat to enable the entire tabs to move backwards, taking out the tabs, and after the tabs are taken out, taking out the detection kits from the casings, and separating the casings fixed together.

Compared with the prior art, the detection apparatus and the detection method thereof have the following advantages:

1. The detection range of the detection apparatus is broad, the detection range of the detection apparatus can be adjusted as needed, several casings can be spliced sequentially, the detection kits can be placed in all the casings, and several probe tips can be placed in each of the detection kits, so that the detection apparatus disclosed by the present invention can perform multipoint in-situ detection on the sludge-water interface of a large region.
2. When the detection apparatus is used for detecting the dissolved oxygen at different heights of different positions of the sludge-water interface, in some embodiments of the present invention, a sample of the sludge-water interface does not need to be taken into the detection container, instead, the detection kits are directly immersed in the water where the sludge-water interface to be detected is located, so that the changes in the natural environment around the sludge-water interface are avoided, and the in-situ detection is completely realized.
3. The detection probes are fixed on the tabs and then placed in the detection kits, so that the detection probes are prevented from being exposed outside, and the detection probes can be well protected from suffering from accidental damage;
4. According to some embodiments of the present invention, several detection probes are arranged, and operate at the same time, so that the effect that several probe tips are used for simultaneously detecting the dissolved oxygen at different heights, at different horizontal positions of the same sludge-water interface is achieved, multiple-time repeated detection experiments are avoided, and not only is time saved, but also the real distribution of dissolved oxygen amounts at different heights, at different horizontal positions of the sludge-water interface at a certain time can also be obtained.

5. The detection apparatus can carry out simultaneous wide-range detection of the dissolved oxygen at different heights and horizontal positions of the sludge-water interface, and thus is quick and convenient for use.

BRIEF DESCRIPTION OF THE DRAWINGS

FIG. 8 is a schematic view of each of the tabs with each of the detection probes placed in;

Figure 1:
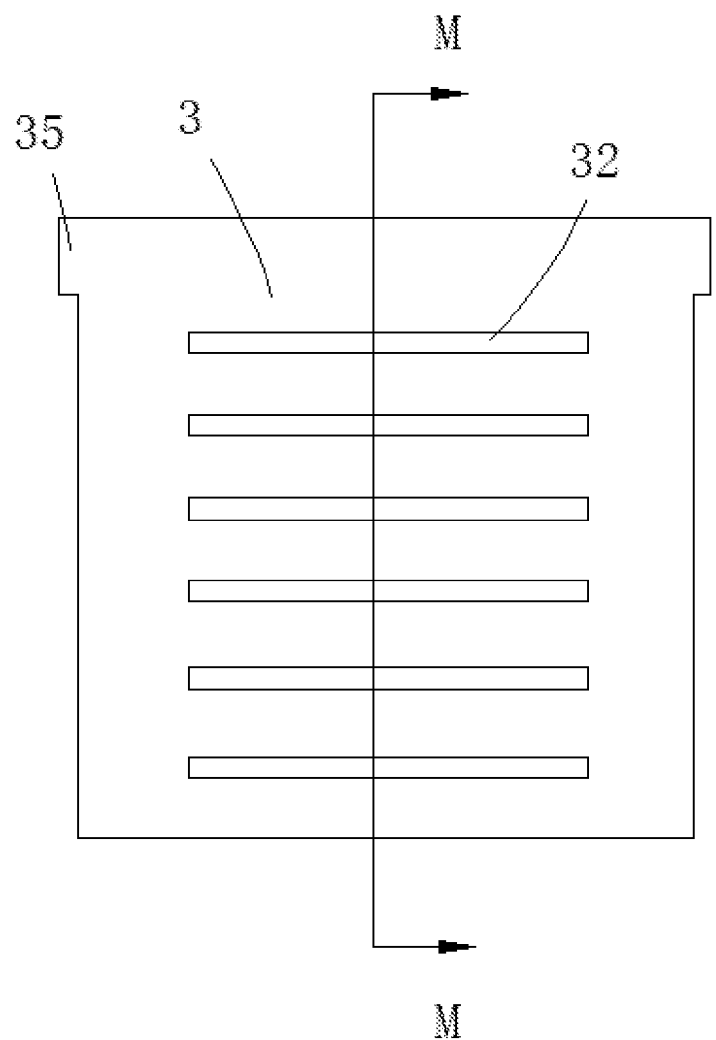
FIG. 1 is a front diagrammatic view showing each of detection kits.

The reference numerals are as follows: Dissolved oxygen shimmer host 1, Detection probe 2, Probe tip 21, Detection kit 3, Water passage chamber 31, Front slot 32, Rear slot 33, Fixing convex 34, Boss body 35, Tab 4, Probe groove 41, Groove window 41*a*, Slip tooth 42, Scales 43, Probe tip pushing structure 5, Pushing tube 51, Front chamber 51*a*, Rear chamber 51*b*, Pushing column 52, Friction block 53, Seal ring 54, Pushing handle 55, Tube rear seat 56, Through window 57, Casing 6, Seat chamber 61, Casing front slot 62, Casing rear slot 63, Fixing shoulder 64, Coupling convex 65, Coupling concave 66.

DETAILED DESCRIPTION OF THE INVENTION

The embodiments of the present invention are further described in connection with the drawings.

Figure 2:
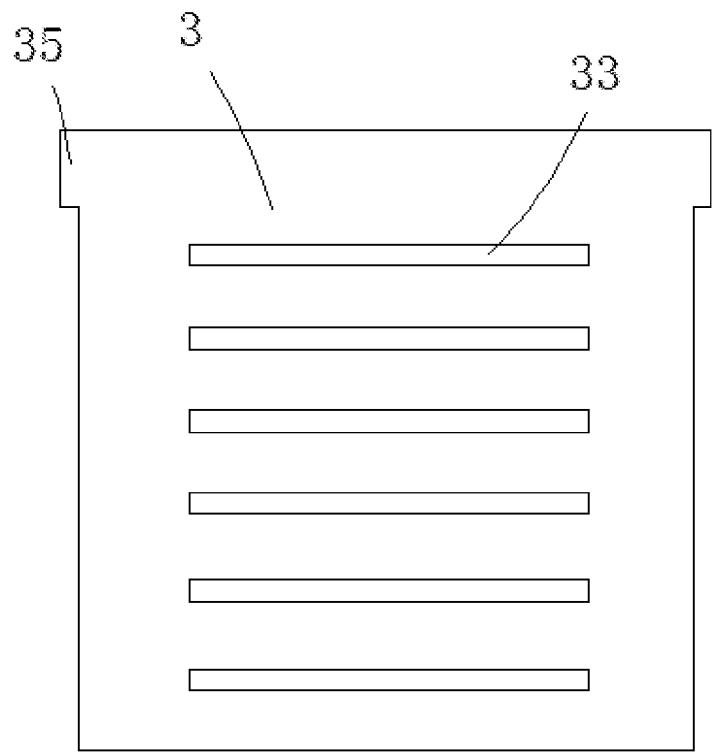
FIG. 2 is a reverse diagrammatic view showing each of the detection kits.
Figure 3:
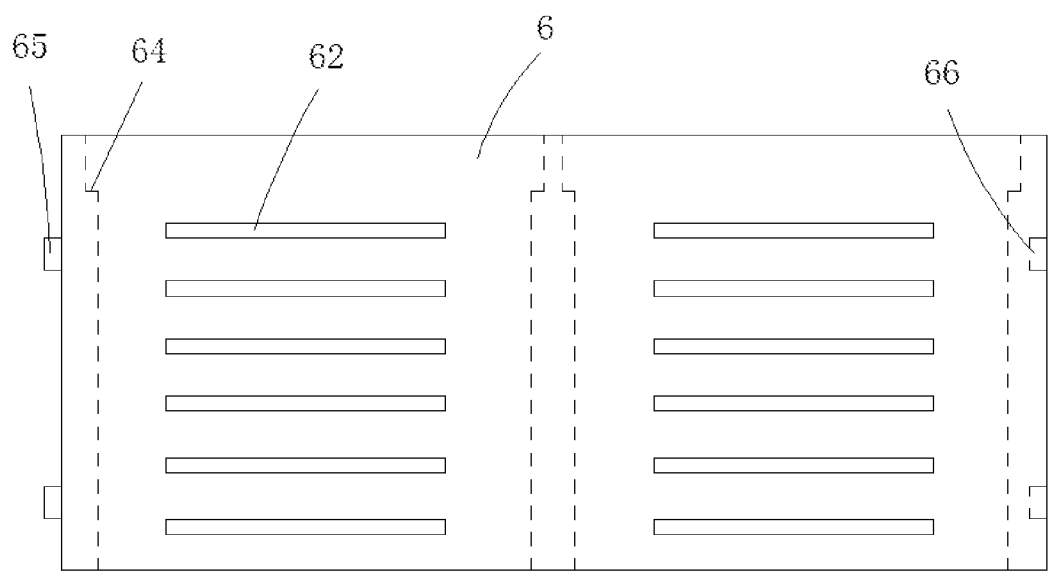
FIG. 3 is a front diagrammatic view showing each of casings.
Figure 4:
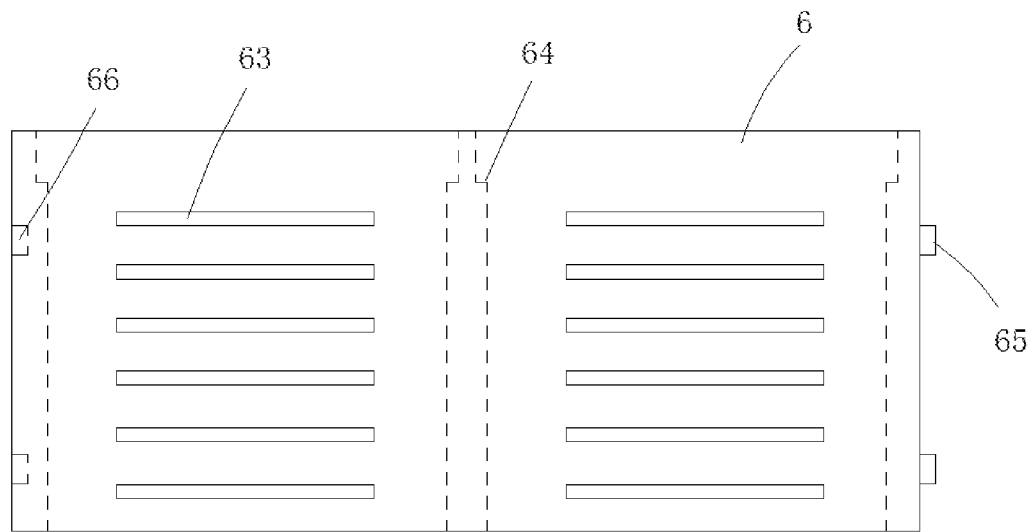
FIG. 4 is a reverse diagrammatic view showing each of the casings.
Figure 5:
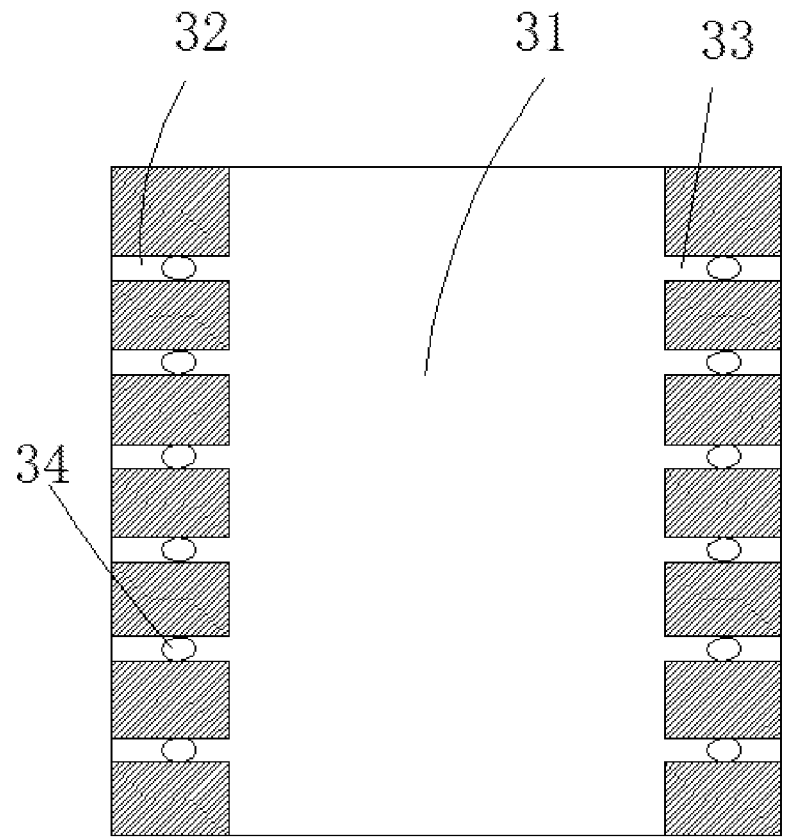
FIG. 5 is an M-M cutaway view of FIG. 1.
Figure 6:
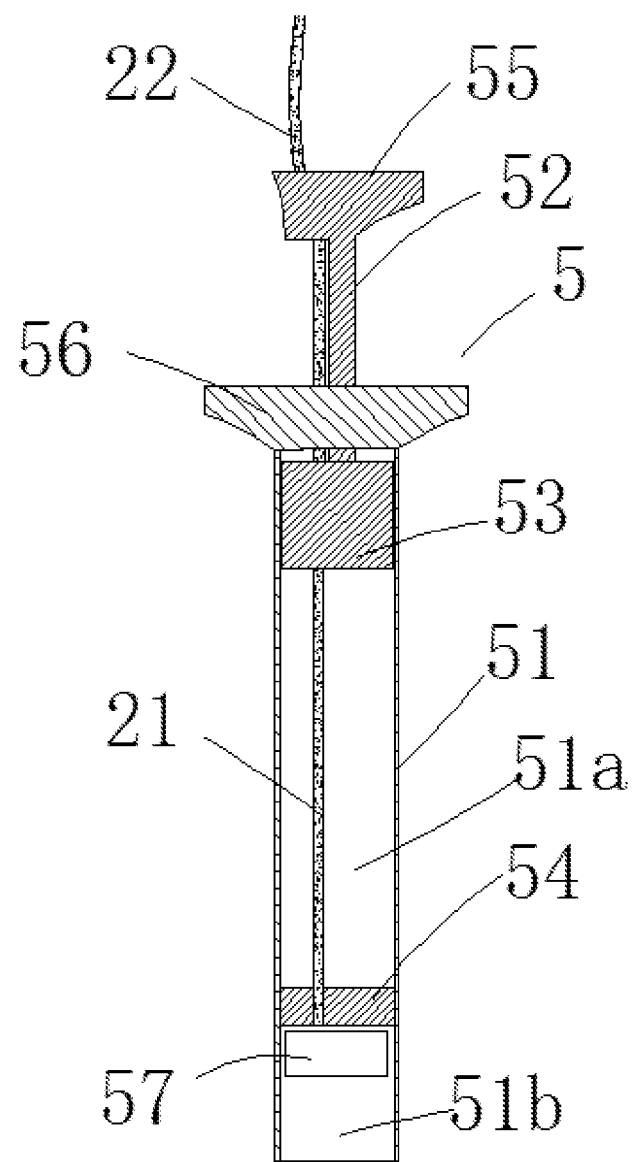
FIG. 6 is a structural view showing each of detection probes.
Figure 7:
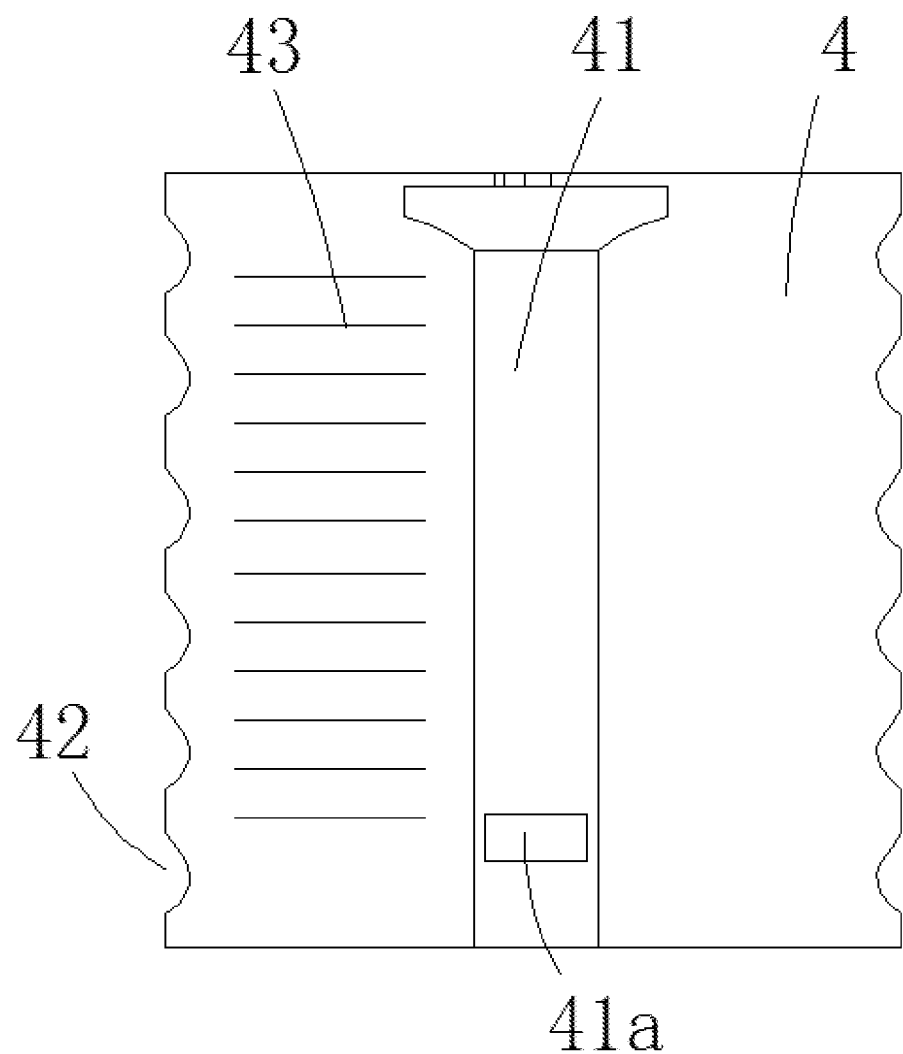
FIG. 7 is a structural view showing each of tabs.
Figure 8:
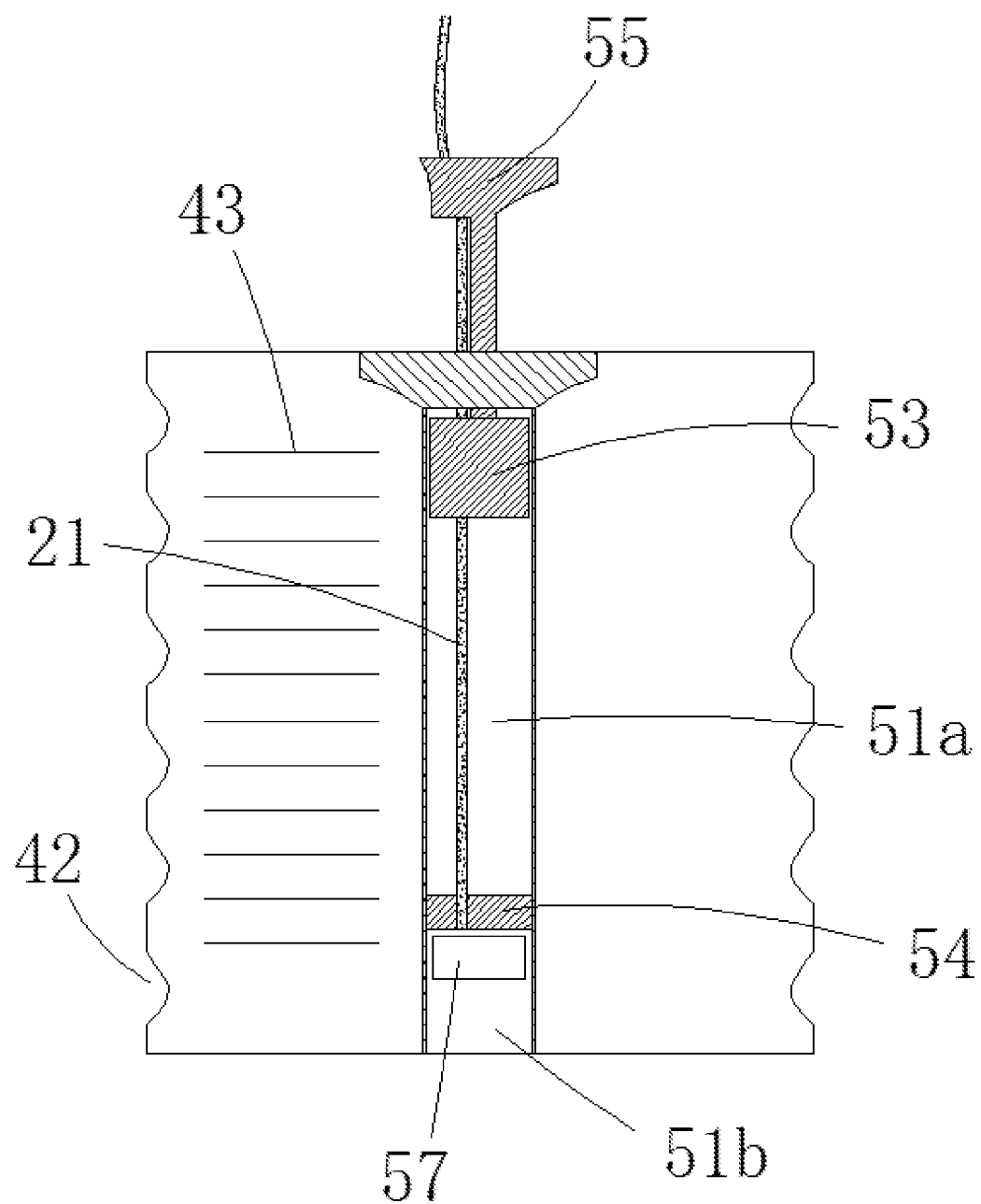
Figure 9:
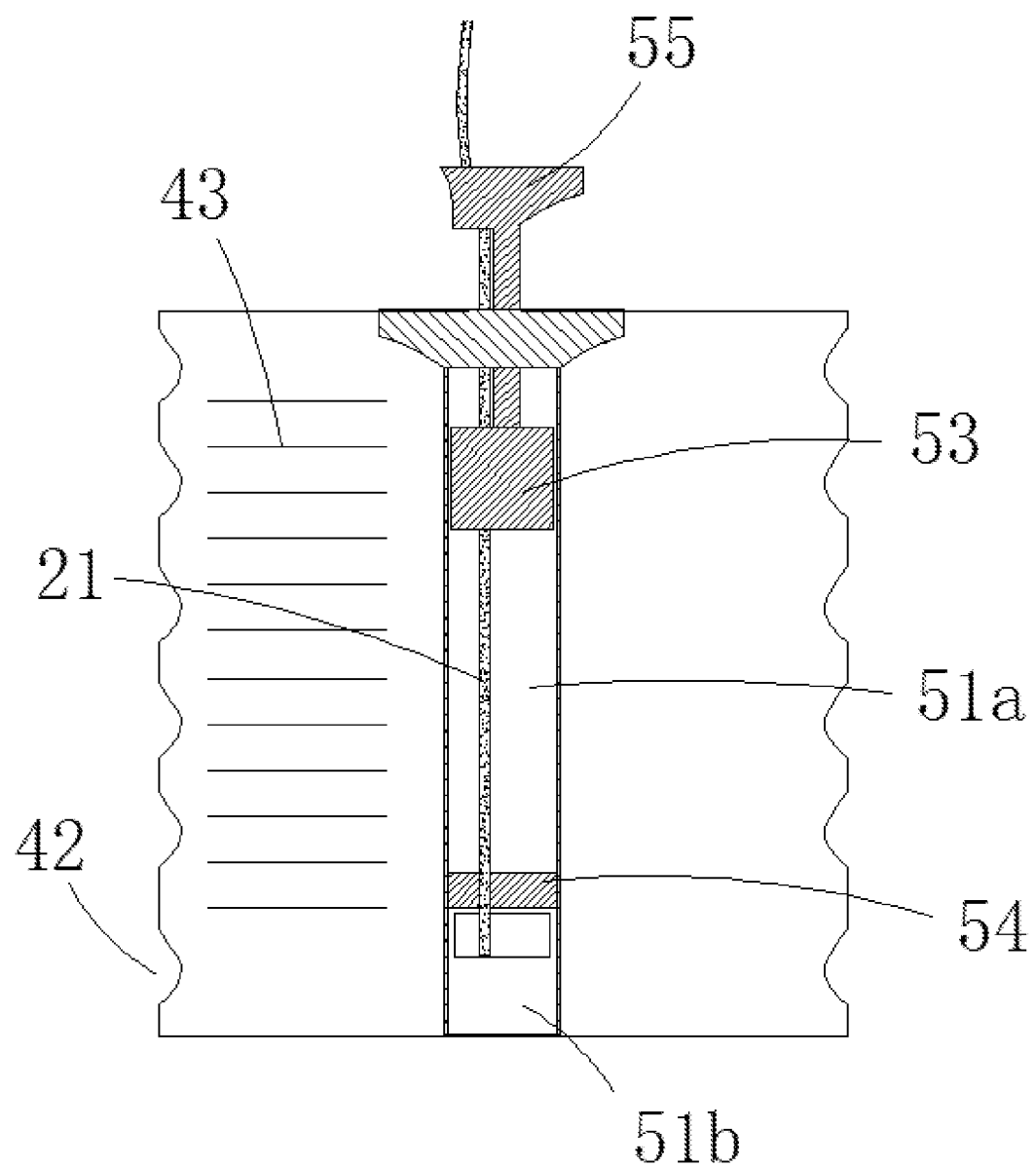
FIG. 9 is a schematic view of each of the probe tips extending outwards.
Figure 10:
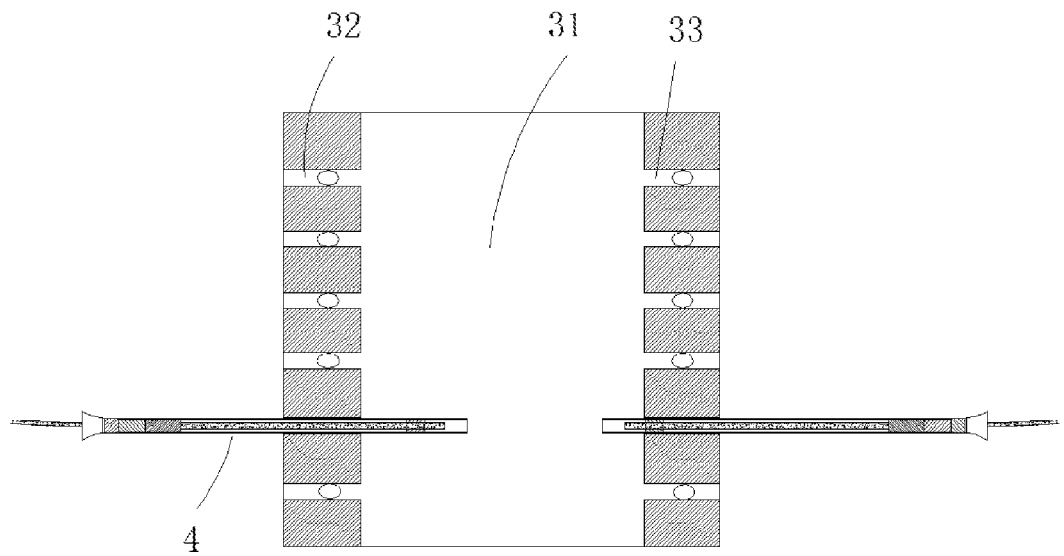
FIG. 10 is a schematic view showing detection of dissolved oxygen of different horizontal positions at the same height of a sludge-water interface.
Figure 11:
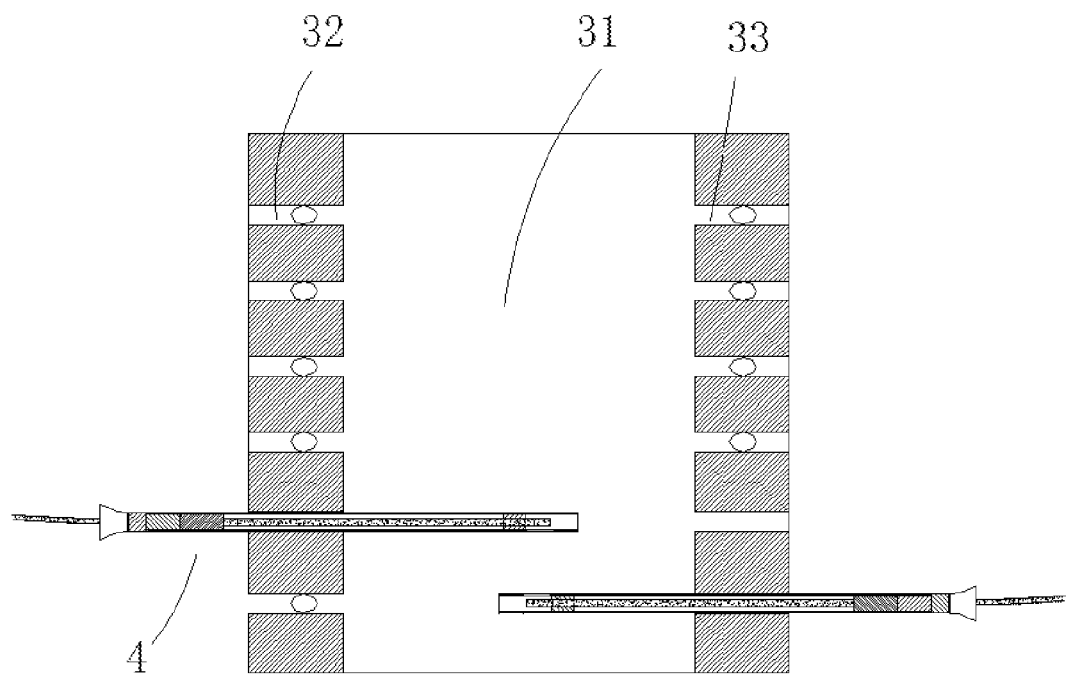
FIG. 11 is a schematic view showing detection of dissolved oxygen at different heights of the same horizontal position of the sludge-water interface.
Figure 12:
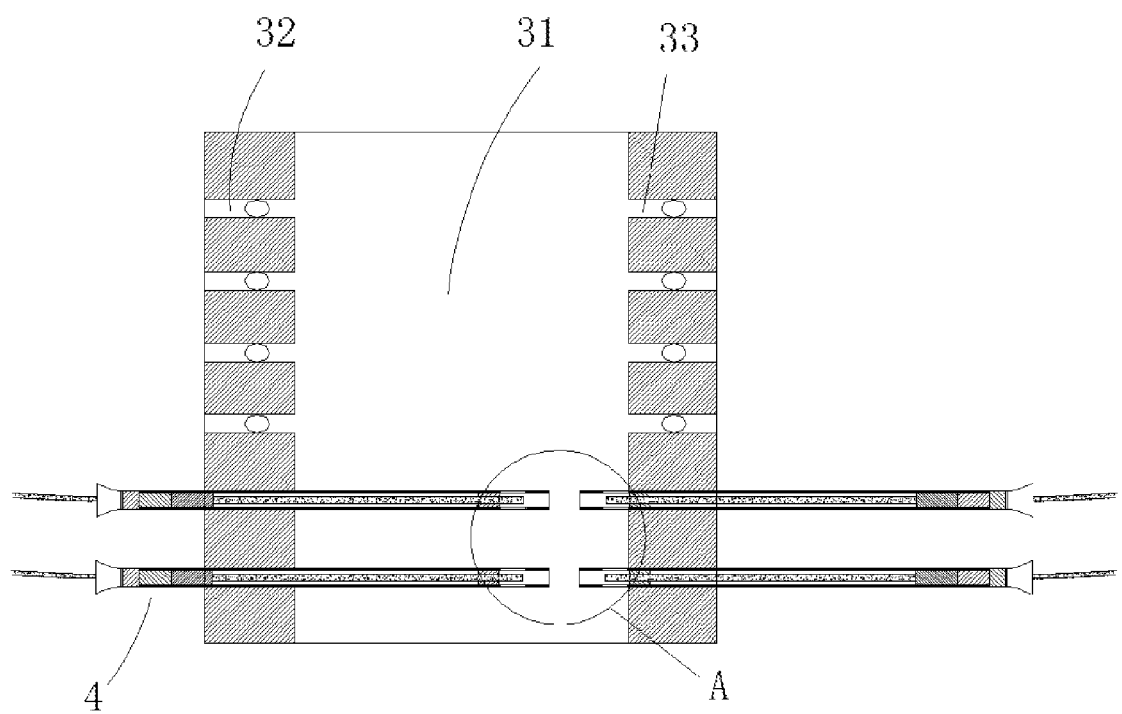
FIG. 12 is a schematic view showing simultaneous detection of dissolved oxygen at different heights and different horizontal positions of the sludge-water interface.
Figure 13:
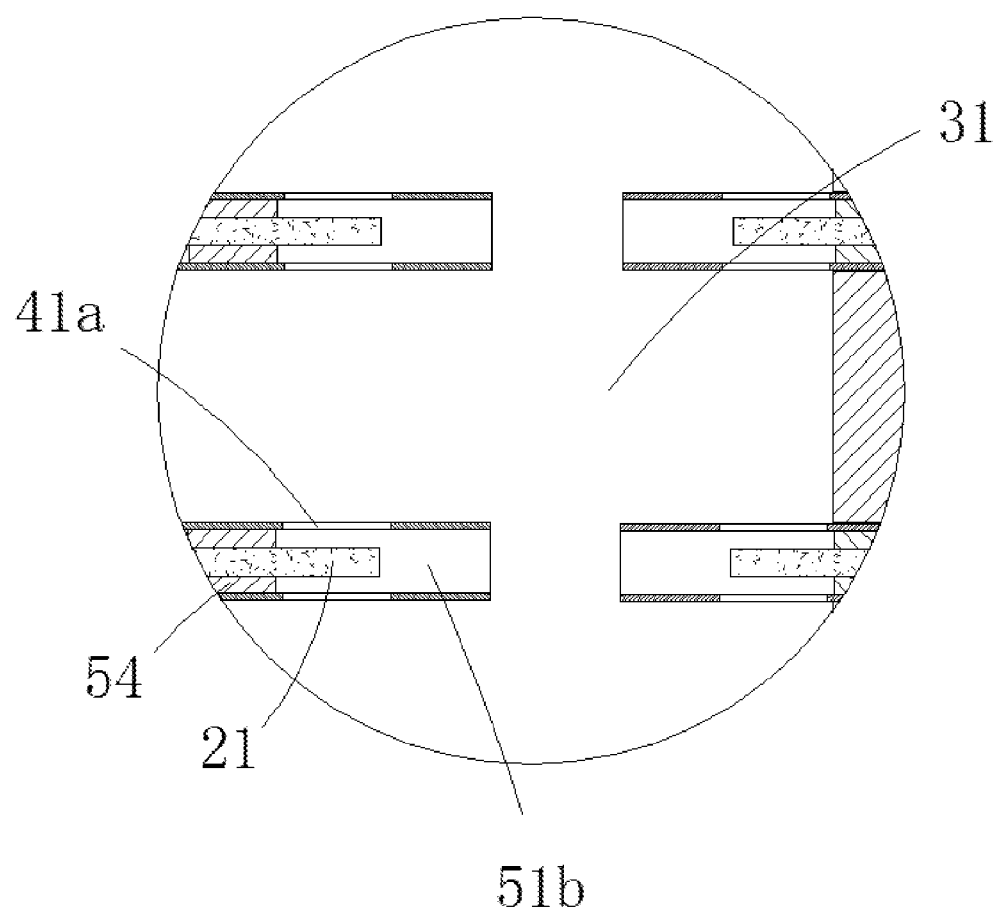
FIG. 13 is an enlarged structural view of part A of FIG. 12.
Figure 14:
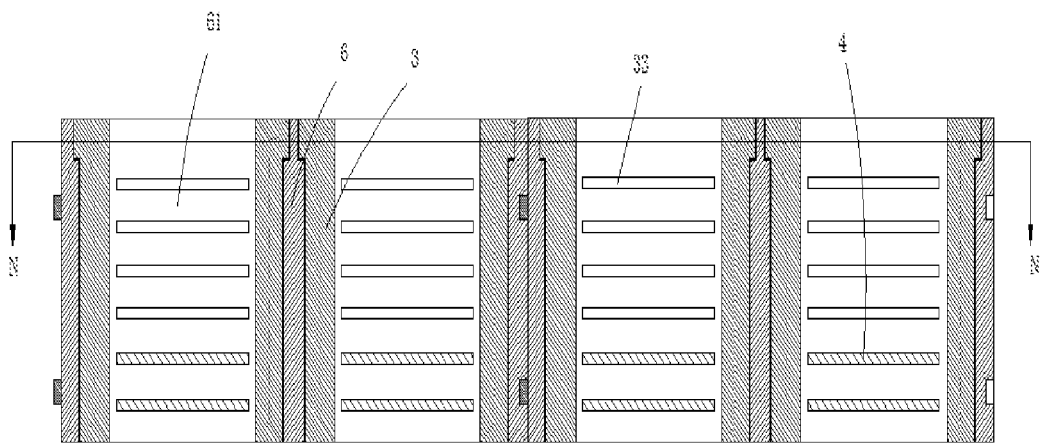
FIG. 14 is a schematic view showing spliced casings.
Figure 15:
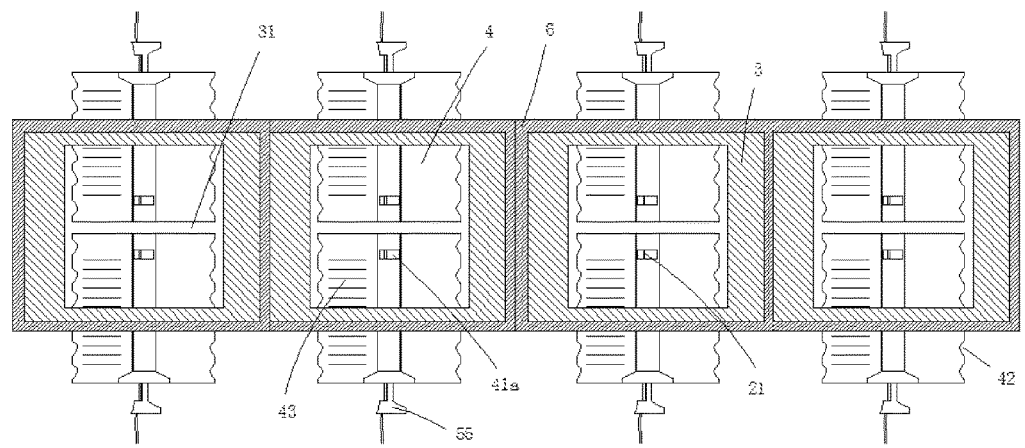
FIG. 15 is an N-N cutaway view of FIG. 14.
Figure 16:
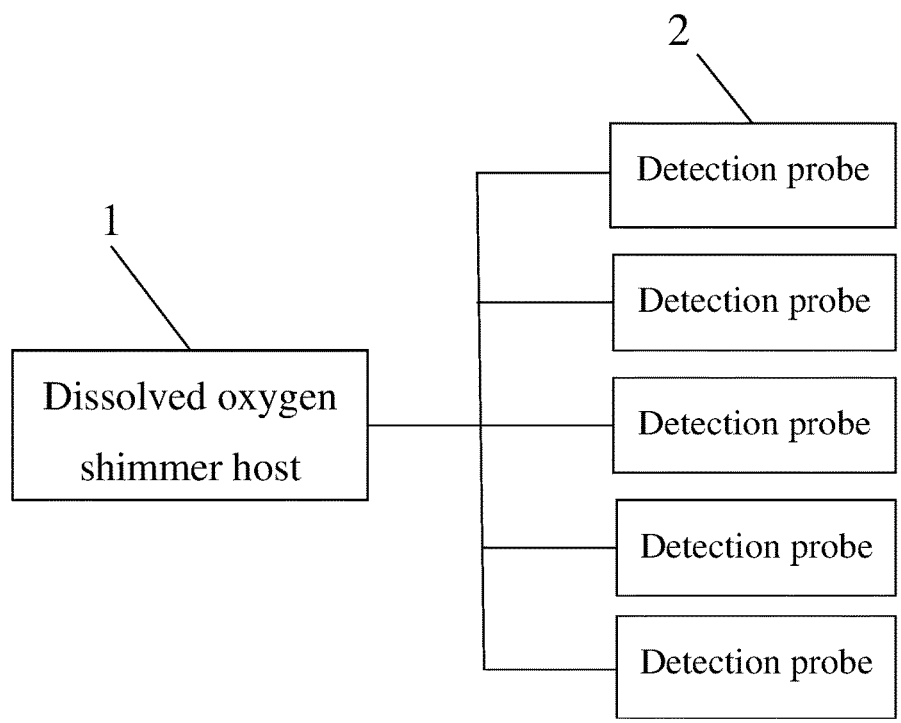
FIG. 16 is a structural schematic block diagram showing the dissolved oxygen shimmer.

As shown in FIG. 1 to FIG. 14, a spliced detection apparatus for simultaneous wide-range in-situ detection of dissolved oxygen in a sludge-water interface comprises a dissolved oxygen shimmer host 1, the dissolved oxygen shimmer host 1 is connected to several detection probes 2, and the detection probes 2 can extend out probe tips 2 for detecting dissolved oxygen; the detection apparatus further comprises a casing 6 and detection kits 3, with several vertically through seat chambers 61 disposed in the casing 6, the detection kits 3 can be placed and fixed in the seat chambers 61, the casing 6 is provided with several horizontally through casing front slots 62 and casing rear slots 63 respectively at the front side and the rear side of each seat chamber 61, the casing front slots 62 and the casing rear slots 63 have correspondingly matching number and height, each of the detection kits 3 is provided with a vertically through water passage chamber 31, while the front side face and the back side face of the detection kit 3 are respectively provided with several detection kit front slots 32 and detection kit rear slots 33 horizontally extending into the detection kit 3; when the detection kit 3 is fixed in the seat chamber 61, the casing front slots 62 and the detection kit front slots 32 are aligned, while the casing rear slots 63 and the detection kit rear slots 33 are aligned; when the casing 6 is placed on the sludge-water interface, the lower portion of the detection kit 3 placed in the seat chamber 61 also comes into contact with the sludge-water interface, and both the detection kit front slots 32 and the detection kit rear slots 33 are in communication with the water passage chamber 31; the detection apparatus further comprises tabs 4, with probe grooves provided on the tabs 4, with the profile of the probe grooves 41 matching the profile of the detection probes 2, each detection probe 2 can be put into the probe groove 41 of the corresponding tab 4 and fixed therein, the tabs 4 can be inserted through the casing slots into the detection kit slots and can enable the probe tips 21 of the detection probes 2 to be placed in the water passage chamber 31; when two tabs 4 are respectively inserted into the detection kit front slot 32 and the detection kit rear slot 33 at the same height, the detection apparatus can detect the dissolved oxygen of different horizontal positions at the same height of the sludge-water interface; when the two tabs 4 are respectively inserted into the detection kit front slots 32 or the detection kit rear slots 33 at different heights, and with the same depth, the detection apparatus can detect the dissolved oxygen of the same horizontal position at different heights of the sludge-water interface; simultaneous detection on different positions of the sludge-water interface can be achieved by fixing several detection kits 3 within the casing 6.

In the embodiments, the casing 6 is provided with a fixing shoulder 64 on the upper portion of each of the seat chambers 61, and accordingly, the upper end of the detection kit 3 is provided with a boss body 35 which is clamped on the fixing shoulder 64 so as to fix the detection kit 3 into the seat chamber 61.

In the embodiments, left and right sides of each of the casing 6 are provided with a coupling convex 65 and a coupling concave 66 respectively, different casings 6 can be connected and fixed together through the clamping between the coupling convex 65 and the coupling concave 66, thus forming a casing assembly, and increasing the detection range in the sludge-water interface.

In the embodiments, a fixing convex 34 is disposed in each of the detection kit front slot 32 and the detection kit rear slot 33; slip teeth 42 are disposed at the edges of each tab 4; when the tab 4 is inserted into the detection kit front slot 32 or the detection kit rear slot 33, the depth of the tab 4 inserted into the slot may be adjusted by selecting different slip teeth 42 for clamping with the fixing convex 34.

In the embodiments, the tabs 4 are marked with the scales 43, and the depth of the tabs 4 inserted into the slots can be read out from the scales 43.

In the embodiments, each of the detection probes 2 comprises a flexible optical fiber 22 and a rigid optical fiber (i.e. the probe tip 21), and the rear end of the rigid optical fiber is connected to the dissolved oxygen shimmer host 1 through the flexible optical fiber 22.

In the embodiments, each of the detection probes 2 further comprises a probe tip pushing structure 5, and the probe tip pushing structure comprises a pushing tube 51, a pushing column 52, a friction block 53, a seal ring 54, a pushing handle 55 and a tube rear seat 56, wherein the pushing handle 55 is connected to the rear end of the pushing column 52, while the front end of the pushing column 52 extends into the pushing tube 51 to be fixedly connected to the friction block 53 in the pushing tube 51; the friction block 53 frictionally engages with the inner wall of the pushing tube 51, and the tube rear seat 56 plugs the rear end of the pushing tube 51; the friction block 53 is fixedly connected to the rear portion of the probe tip 21, and the seal ring 54 is fixed in the pushing tube 51 to separate a chamber of the pushing tube 51 into a front chamber 51a and a rear chamber 51b in a sealing manner, with the front chamber 51a being provided with a through window 57 through which water can enter the front chamber 51a, and accordingly, each probe groove 41 is provided with a groove window 41a at the position corresponding to the through window 57; when the tab 4 for fixing the detection probe 2 is positioned in the water passage chamber 31, the through window 57 is in communication with the water passage chamber 31 through the groove window 41a; when an external force for pushing the pushing handle 55 is greater than the frictional force between the friction block 53 and the pushing tube 51, the friction block 53 slides in the pushing tube 51, so that the probe tip 21 extends into the front chamber 51a.

In the embodiments, the flexible optical fiber 22 is fixedly connected to the pushing handle 55.

The detection method for simultaneous wide-range in-situ detection of dissolved oxygen in the sludge-water interface comprises the following steps:

step a, assembling a detection apparatus: based on the size of the sludge-water interface to be detected, selecting casings 6 and detection kits 3 of appropriate numbers, fixedly connecting the casings 6 in turn, placing and fixing the detection kits 3 in seat chambers 61 of the casings 6 to ensure that corresponding casing front slots 62 and detection kit front slots 32 are aligned, while casing rear slots 63 and detection kit rear slots 33 are aligned, then selecting several detection probes as needed, clamping each detection probe 2 into the probe groove 41 of the corresponding tab 4 to ensure that the detection probes 2 and the tabs 4 are positioned;

step b, detecting the dissolved oxygen of different horizontal positions at the same height of the sludge-water interface: selecting a pair of the detection kit front slot 32 and the detection kit rear slot 33 at the same height, and respectively enabling the tabs 4 to insert through the corresponding casing slots into the detection kit front slot 32 and the detection kit rear slot 33, so as to push the probe tip 21 of each of the detection probes 2 to the front chamber 51a of the pushing tube 51; depositing the assembled casing 6 onto the sludge-water interface, injecting water into the water passage chamber 31 and the front chamber 51a of the pushing tube 51, and collecting the data of dissolved oxygen in water through each probe tip 21;

step c, detecting the dissolved oxygen at different heights in the same horizontal position of the sludge-water interface: selecting several detection kit front slots 32 and/or detection kit rear slots 33, positioned at different heights, respectively enabling the tabs 4 to insert through the corresponding casing slots into the selected detection kit front slots 32 and/or detection kit rear slots 33, adjusting the depth of the tabs 4 inserted into the detection kit front slots 32 and/or the detection kit rear slots 33, then pushing the probe tip 21 of each of the detection probes 2 to the front chamber 51a of the pushing tube 51 to enable each of the probe tips 21 to be positioned at different heights in the same horizontal position, depositing the assembled casing 6 onto the sludge-water interface, injecting water into the water passage chamber 31 and the front chamber 51a of the pushing tube 51, and collecting the data of dissolved oxygen in water through each probe tip 21;

step d, simultaneously detecting the dissolved oxygen at different horizontal positions and different heights of the sludge-water interface; simultaneously performing step b and step c;

step e, transmitting the data of dissolved oxygen collected by the probe tips 21 in step b, step c and step d to the dissolved oxygen shimmer host 1, and the dissolved oxygen shimmer host 1 performing analysis treatment on the data and then displaying the data;

step f, lifting the casings 6 from water and taking out the tabs 4 after detection, wherein the method for taking out the tabs 4 comprises the following steps of pulling the pushing handle 55 backwards, so that the friction block 53 slides backwards, when the friction block 53 slides to the rear end of the pushing tube 51, enabling the probe pins 21 to be retracted into the rear chamber 51b of the pushing tube 51, continuously pulling the pushing handle 55 backwards to enable the friction block 53 to push against the tube rear seat 56 to enable the entire tabs 4 to move backwards, taking out the tabs 4, and after the tabs 4 are taken out, taking out the detection kits 3 from the casings 6, and separating the casings 6 fixed together.

According to the present invention, the detection kits 3 are thin, the height of each of the detection kits 3 does not exceed 1 cm, and the thickness of each of the tabs 4 is about 1 mm.

In the embodiments, the adopted detection probes 2 are fluorescent probes which detect the sludge-water interface by using the principle that the dissolved oxygen shimmer host 1 is used for emitting laser, which is emitted to the probes 21 through the flexible optical fiber 22; an oxygen fluorescent sensitive material is arranged at the front end of each of the probe tips 21, on which the laser is emitted; fluorescence generated through a fluorescence quenching effect is fed back to the dissolved oxygen shimmer host 1, which converts fluorescent signals into electrical signals, and demodulates the electrical signals, and then the demodulated electrical signals are compared with a dissolved oxygen concentration change relation, so that the dissolved oxygen concentration information is obtained. The oxygen fluorescent sensitive material can be selected from various fluorescent sensitive materials in the prior art, wherein the preferable material is a ruthenium complex, such as $Ru(dpp)_3Cl_2$.

Those above are the preferred embodiments of the present invention only, and the protective scope of the present invention is not limited to the embodiments, and technical solutions within the spirit of the present invention belong to the protective scope of the present invention. It should be noted that various modifications and equivalent arrangements without departing from the principle of the present invention should be defined to be within the protective scope of the present invention for those skilled in the art.

What is claimed:

1. A spliced detection apparatus for simultaneous wide-range in-situ detection of dissolved oxygen in a sludge-water interface, comprising a dissolved oxygen shimmer host and a plurality of detection probes connected thereto capable of extending out probe tips for detecting dissolved oxygen, wherein the spliced detection apparatus further comprises a casing and detection kits; the casing is disposed therein with a plurality of vertically through seat chambers, in which the detection kits can be placed and fixed; the casing is provided with a plurality of horizontally through casing front slots and casing rear slots respectively at a front side and a rear side of each of the seat chambers, which have corresponding number and height; each of the detection kits is provided thereon with a vertically through water passage chamber, and is respectively provided with a plurality of detection kit front slots and detection kit rear slots horizontally extending into the detection kit in a front side face and a back side face; when the detection kit is fixed in the seat chamber, the casing front slots and the detection kit front slots are aligned, and the casing rear slots and the detection kit rear slots are aligned; when the casing is placed on the sludge-water interface, a lower portion of the detection kit placed in the seat chamber also comes into contact with the sludge-water interface, and both the detection kit front slots and the detection kit rear slots are in communication with the water passage chamber; the detection apparatus further comprises tabs, provided thereon with probe grooves which have a profile adapt to the profile of the detection probes; each of the detection probes can be put into the probe groove of the corresponding tab and fixed therein; the tabs can be inserted through the casing slots into the detection kit slots and enable the probe tips of the detection probes to be placed in the water passage chamber; when two tabs are respectively inserted into the detection kit front slot and the detection kit rear slot at the same height, the detection apparatus can detect the dissolved oxygen in different horizontal positions at the same height of the sludge-water interface; when the two tabs are inserted into the detection kit front slots or the detection kit rear slots at different heights yet with the same depth, the detection apparatus can detect the dissolved oxygen in the same horizontal position at different heights of the sludge-water interface; thus the sludge-water interface can be simultaneously detected in different positions by fixing several detection kits within the casing.

2. The spliced detection apparatus for simultaneous wide-range in-situ detection of dissolved oxygen in a sludge-water interface according to claim 1, wherein the casing is provided with a fixing shoulder on an upper portion of each seat chamber, and accordingly, the detection kit is provided with a boss body at an upper end, which is clamped on the fixing shoulder so as to fix the detection kit into the seat chamber.

3. The spliced detection apparatus for simultaneous wide-range in-situ detection of dissolved oxygen in a sludge-water interface according to claim 2, wherein the casing are provided with a coupling convex and a coupling concave respectively at left and right sides, so that different casings can be connected and fixed together through the clamping between the coupling convex and the coupling concave, thus forming a casing assembly, and increasing the detection range in the sludge-water interface.

4. The spliced detection apparatus for simultaneous wide-range in-situ detection of dissolved oxygen in a sludge-water interface according to claim 3, wherein a fixing convex is disposed in each of the detection kit front slot and the detection kit rear slot, and slip teeth are disposed at the edges of each tab; when the tab is inserted into the detection kit front slot or the detection kit rear slot, a depth of the tab inserted into the slot is adjusted by selecting different slip teeth to clamp with the fixing convex.

5. The spliced detection apparatus for simultaneous wide-range in-situ detection of dissolved oxygen in a sludge-water interface according to claim 4, wherein each of the tabs is marked with a scale, and the depth of the tab inserted into the slot can be read out from the scale.

6. The spliced detection apparatus for simultaneous wide-range in-situ detection of dissolved oxygen in a sludge-water interface according to claim 5, wherein each of the detection probes comprises a flexible optical fiber and a rigid optical fiber which is the probe tip, and the rigid optical fiber is connected to the dissolved oxygen shimmer host at an rear end through the flexible optical fiber.

7. The spliced detection apparatus for simultaneous wide-range in-situ detection of dissolved oxygen in a sludge-water interface according to claim 6, wherein each of the detection probes further comprises a probe tip pushing structure, which comprises a pushing tube, a pushing column, a friction block, a seal ring, a pushing handle and a tube rear seat, wherein the pushing handle is connected at a rear end of the pushing column; a front end of the pushing column extends into the pushing tube to be fixedly connected to the friction block in the pushing tube; the friction block frictionally engages with an inner wall of the pushing tube; the tube rear seat plugs the rear end of the pushing tube; the friction block is fixedly connected to the rear portion of the probe tip; the seal ring is fixed in the pushing tube to separate the chamber of the pushing tube into a front chamber and a rear chamber in a sealing manner; the front chamber is provided with a through window through which water can enter the front chamber, and accordingly, each of the probe groove is provided with a groove window at the position corresponding to the through window; when the tab fixing the detection probe is positioned in the water passage chamber, the through window is in communication with the water passage chamber through the groove window; when an external force for pushing the pushing handle is greater than the frictional force between the friction block and the pushing tube, the friction block slides within the pushing tube, so that the probe tip extends into the front chamber.

8. The spliced detection apparatus for simultaneous wide-range in-situ detection of dissolved oxygen in a sludge-water interface according to claim 7, wherein the flexible optical fiber is fixedly connected to the pushing handle.

9. A detection method for simultaneous wide-range in-situ detection of dissolved oxygen in a sludge-water interface, comprising the following steps:
  step a: assembling a detection apparatus: based on the size of the area of the sludge-water interface to be detected, selecting an appropriate number of casings and detection kits, fixedly connecting the casings in turn, placing into and fixing the detection kits in seat chambers of the casings to ensure that corresponding casing front slots and detection kit front slots are aligned, and casing rear slots and detection kit rear slots are aligned, and then selecting several detection probes as needed, clamping each detection probe into a probe groove of the corresponding tab to ensure that the detection probes and the tabs are positioned;
  step b: detecting the dissolved oxygen in different horizontal positions at the same height of the sludge-water interface, comprising: selecting a pair of the detection kit front slot and the detection kit rear slot at the same height, and respectively enabling the tabs to insert through the corresponding casing slots into the detection kit front slot and the detection kit rear slot, so as to push the probe tip of each of the detection probes to the front chamber of the pushing tube; depositing the assembled casing onto the sludge-water interface, pouring water into the water passage chamber and the front chamber of the pushing tube, and collecting the data of dissolved oxygen in water through each probe tip;

step c: detecting the dissolved oxygen at different heights in the same horizontal position of the sludge-water interface, comprising: selecting several detection kit front slots and/or detection kit rear slots positioned at different heights, respectively enabling the tabs to insert through the corresponding casing slots into the selected detection kit front slots and/or detection kit rear slots, adjusting the depth of the tabs inserted into the detection kit front slots and/or the detection kit rear slots, then pushing the probe tip of each of the detection probes to the front chamber of the pushing tube to enable each of the probe tips to be positioned at different heights in the same horizontal position, depositing the assembled casing onto the sludge-water interface, pouring water into the water passage chamber and the front chamber of the pushing tube, and collecting the data of dissolved oxygen in water through each probe tip;

step d: simultaneously detecting the dissolved oxygen in different horizontal positions and at different heights of the sludge-water interface by simultaneously performing step b and step c; and step e: transmitting the data of dissolved oxygen collected by the probe tips in step b, step c and step d to the dissolved oxygen shimmer host, and displaying a result after the dissolved oxygen shimmer host performs analysis treatment on the data.

10. The detection method for simultaneous wide-range in-situ detection of dissolved oxygen in a sludge-water interface according to claim 9, further comprising a step f: lifting the casings from water and taking out the tabs after detection, wherein the method for taking out the tabs comprises the following steps of pulling the pushing handle backwards, so that the friction block slides backwards, when the friction block slides to the rear end of the pushing tube, enabling the probe tips to be retracted into the rear chamber of the pushing tube, further pulling the pushing handle backwards to enable the friction block to push against the tube rear seat to enable the entire tabs to move backwards, taking out the tabs, and after the tabs are taken out, taking out the detection kits from the casings, and separating the casings fixed together.

* * * * *